United States Patent [19]

Sneider

[11] 4,274,555
[45] Jun. 23, 1981

[54] FLEXIBLE SYRINGE WITH NOZZLE CLOSURE

[76] Inventor: Vincent R. Sneider, 3422 Hallcrest Dr., Atlanta, Ga. 30319

[21] Appl. No.: 967,462

[22] Filed: Dec. 7, 1978

[51] Int. Cl.³ .......................... A61M 1/00; A61M 7/02
[52] U.S. Cl. .................................... 222/107; 128/231; 128/251; 222/566
[58] Field of Search ................. 222/92, 107, 566, 567, 222/568, 569, 570; 150/8; 128/231, 232, 248, 251, 258, 403, DIG. 24; 292/256.6

[56] References Cited

U.S. PATENT DOCUMENTS

| 541,639 | 6/1895 | Smith | 128/231 |
|---|---|---|---|
| 3,308,998 | 3/1967 | Oppasser et al. | 222/569 X |
| 3,754,553 | 8/1973 | Hewitt et al. | 128/232 |
| 3,771,523 | 11/1973 | Zanca | 128/232 |

*Primary Examiner*—David A. Scherbel
*Attorney, Agent, or Firm*—Ralph R. Roberts

[57] ABSTRACT

A closure for a syringe of the feminine type wherein the nozzle of the syringe is intended to be transported separately from the flexible bag. The bag has a neck portion with a passageway adapted to receive the head of a faucet for purposes of filling the bag. The neck includes a flexible washer section and also a wall section surrounding the passageway into the neck. A hollow nozzle member has a hollow stem portion and the lower inlet end thereof has outwardly extending tooth portions and said stem portion is dimensioned to be placed in the neck portion. An outwardly extending ring portion is formed on the stem portion of the nozzle member and engages the washer section surrounding the passageway. A ring-like member is formed on the nozzle stem and in a second embodiment extends outwardly from the nozzle member and in proximity to the nozzle inlet end seats in a like sized groove formed in the neck portion of the bag. The lower tooth portions on the stem in an inserted and mounted condition in the first embodiment engages a wall section inside the bag to provide a fluid-tight engagement and a fitment so that that once the nozzle member is inserted into the neck it can only be removed with extreme difficulty.

8 Claims, 9 Drawing Figures

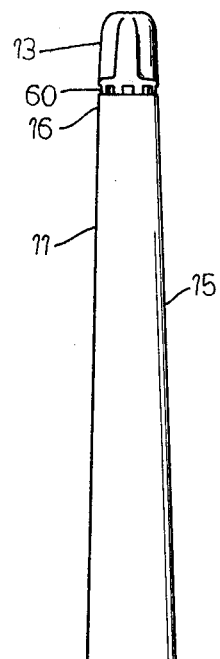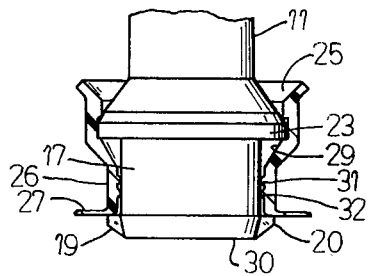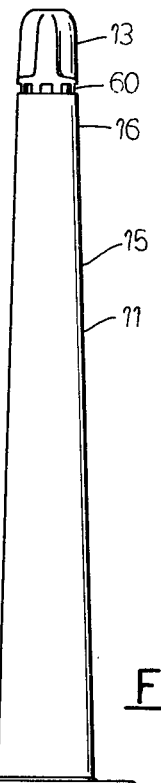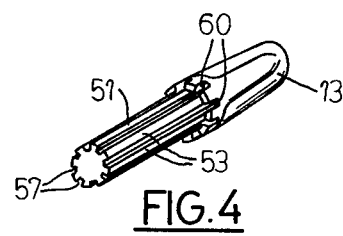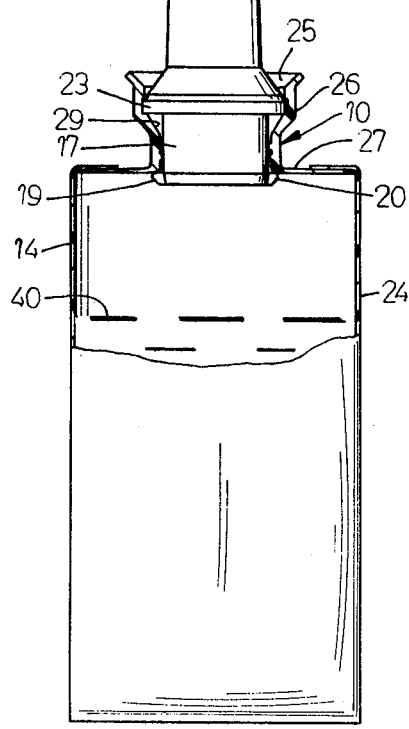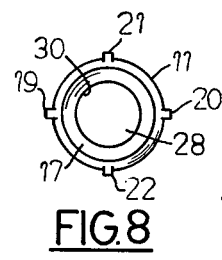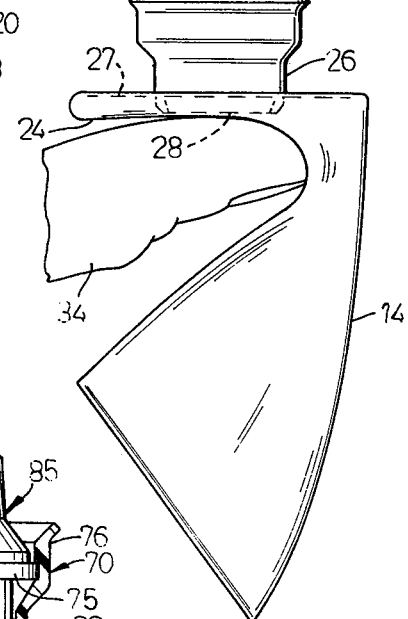

FLEXIBLE SYRINGE WITH NOZZLE CLOSURE

BACKGROUND OF THE INVENTION

This invention relates to a closure means for a feminine syringe. More particularly, this invention relates to a connection means for a disposable syringe wherein the nozzle member has a projection which will sealably engage the neck of the syringe bag and will prevent the removal of the syringe nozzle.

Closure means for the types of syringe bags concerned with in this invention are described in U.S. Pat. Nos. 3,667,461; 3,754,553; 3,771,523 and 3,844,284. In U.S. Pat. No. 3,771,523 a tapering portion is provided on a nozzle with either an undercut or an annulus for engagement with a complementary annulus or undercut in the container collar. In U.S. Pat. No. 3,754,553 circumferential lips are utilized for engaging the end of a sleeve for prevention of removal of a plug from the sleeve. In U.S. Pat. No. 3,667,461 a clamping ring is utilized to make a connection between a syringe bag and a spray nozzle. A collapsible syringe unit is described in U.S. Pat. No. 3,844,284 wherein a threaded connection is utilized between the nozzle and the syringe container.

The prior art nowhere describes a disposable syringe unit wherein the neck of the bag will receive the head of a faucet in a fluid-tight engagement and subsequently receive a nozzle member also in a fluid-tight manner and such that the nozzle can be removed only with extreme difficulty. Further, the connection means of the present invention also affords a unique valving action whereby the finger of a hand can press the flexible bag against the inlet of the bag neck which is facilitated by utilizing an extending wall section which surrounds the neck passageway and serves as a means of connection with the flexible wall of the bag.

It is an advantage of the present invention to provide a novel closure means for a feminine syringe bag. Other advantages include a connection for a disposable syringe bag wherein the nozzle is packaged separately from the syringe bag and is received in the neck of the container in a fluid-tight manner and cannot easily be removed therefrom; a connector which will receive the head of a faucet in a fluid-tight manner as well as a hollow nozzle member; a disposable syringe bag wherein the neck is formed with a wall member and connected to the flexible wall of the container such that the wall of the container can be forced against the passageway in the neck to act as a valve; and a connection means for a disposable feminine syringe bag which can be easily molded and fabricated at low cost.

SUMMARY OF THE INVENTION

The foregoing advantages are accomplished and the shortcomings of the prior art are overcome by the present closure means which includes a hollow nozzle member having a hollow spray stem with an outlet and an inlet end. A first projecting means is spaced from the inlet end and extends outwardly from the nozzle member. A syringe bag having a flexible wall or walls is connected to a neck portion which is constructed to receive the inlet end of the nozzle member. A wall section surrounds the passageway and is positioned adjacent the entry into the bag. A flexible washer section is provided inside the neck and in the passageway. A second projecting means extends outwardly from said nozzle member and in proximity to the inlet end or, alternatively, extends inwardly toward the passageway to form a groove. When the inlet end of the nozzle member is placed in the passageway the first projecting means engages the washer section and in one instance the second projecting means will engage the wall section and in another instance the second projecting means will engage the groove so that a fluid-tight, resilient connection is provided between the nozzle and the bag and the nozzle is prevented from being removed therefrom. In one embodiment, the first projecting means is in the form of shark's teeth which will engage the inside of the wall section surrounding the neck passageway. The wall section surrounding the passageway also affords a means in conjunction with the flexible wall section providing a valving action whereby the finger of the hand can press the flexible wall against the passageway in the neck to prevent the flow of liquid. Also, in a preferable manner, the first projecting means is in the form of an annular flange which resiliently engages the flexible washer section of the neck when the second projecting means engages the inside of the wall section surrounding the passageway or the groove.

BRIEF DESCRIPTION OF THE DRAWINGS

A better understanding of the present connection means will be accomplished by reference to the drawings wherein:

FIG. 4 is a perspective view of the nozzle head.

FIG. 5 is a view in side elevation and partially in vertical section showing the nozzle member in engagement with the neck of the syringe bag.

FIG. 6 is an enlarged partial view and in partial vertical section showing the connection between the nozzle and the neck of the syringe bag.

FIG. 7 is a view in side elevation illustrating the valving action provided by pressing the flexible wall of the bag with a finger against the neck passageway.

FIG. 8 is an end view of the inlet end of the nozzle shown in FIGS. 2, 5, 6 and 7.

FIG. 9 is a fragmentary view and partially in vertical section of another embodiment.

DESCRIPTION OF THE EMBODIMENTS

Figure 3:
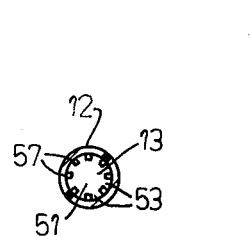
FIG. 3 is a view in horizontal section taken along line 3—3 of FIG. 2.
Figure 1:
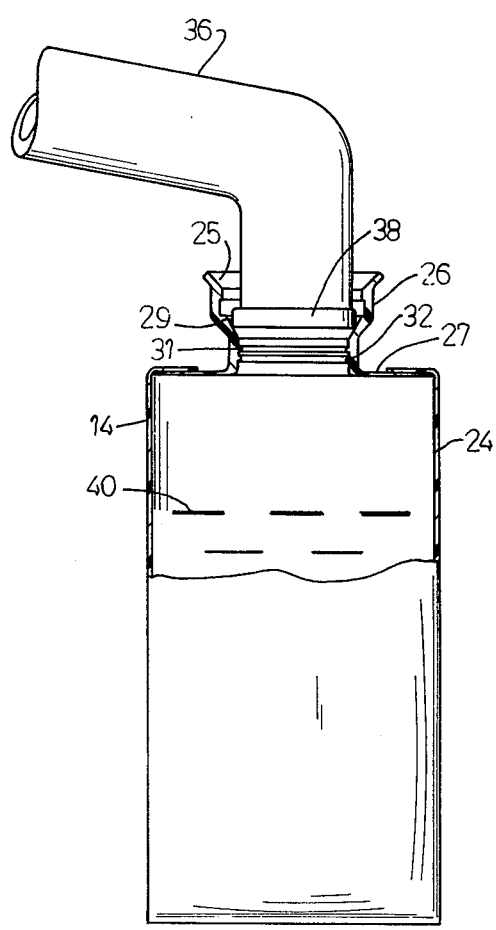
FIG. 1 is a view in side elevation and partially in vertical section showing the head of a faucet engaging the neck of the syringe bag for filling purposes.

Proceeding to a detailed description of one embodiment of the present invention, a syringe bag 14 is shown in FIG. 1 with an annular neck portion 26 receiving the head 38 of a faucet 36 in order to fill the bag with liquid 40. The neck 26 includes a flexible and resilient washer section 29 for resilient and sealable engagement with head 38.

Figure 2:
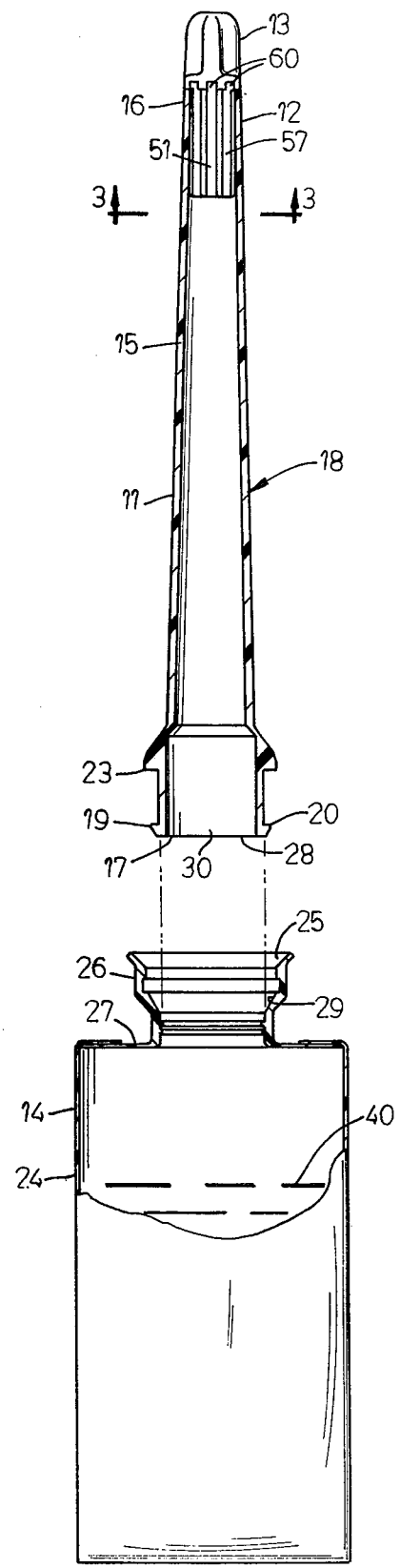
FIG. 2 is a view in side elevation and partially in vertical section showing the syringe bag and the nozzle member spaced therefrom as it would be orientated prior to insertion into the bag neck section.

A nozzle 11 formed from a hollow nozzle wall 12 is shown in FIG. 2 and positioned from the syringe bag 14. The nozzle 11 has a spray stem 15 with an outlet end 16 and an annular inlet end 17. Projecting ledges 19 and 20 extend outwardly from the nozzle member 11 as does a projecting flange 23 spaced from the projecting ledges 19 and 20 and extending in a complete peripheral manner around nozzle 11.

As best seen in FIS. 3 and 4, the nozzle head 13 is formed from a hub 51 which is inserted into the hollow spray section 15. The hub includes a plurality of longitudinally extending ribs 53 which define channels 57 therebetween. A plurality of radiating ports 60 extend from channels 57 and outwardly from head 13. The nozzle structure is the subject matter of U.S. Pat. No. 4,133,313 by the same inventor and entitled "Expandable Syringe and Means for Storing Chemical Agents for Use Therewith."

Referring specifically to FIGS. 5 and 6, it will be seen that the inlet end 17 of nozzle 11 is accommodated by the neck portion 26 of bag 14. As seated therein, projecting ledges 19 and 20 as well as projections 21 and 22 will engage the wall section 27 opposite neck portion 26 and inside bag 14. At the same time, projecting flange 23 will be forced against flexible washer section 29 as the projecting ledges 19–22 are forced under wall section 27. This is effected by having the total distance between projecting ledges 19–22 and projecting flange 23 less than the distance between wall 27 and washer section 29. A pair of sealing rings 31 and 32 are also provided inside neck portion 26 and engage the inlet end 17 of nozzle 11 for added sealing purposes.

Referring to FIG. 7, it will be seen that the use of a flexible wall 24 for bag 14 permits a finger 34 to force a portion of the bag against the passageway 28 of nozzle 11 to thereby effect a valving action. This controlled bending of a portion of a bag against the passageway is facilitated by utilizing a semirigid, annular wall section 27 adjacent neck 26 so as to give some rigidity to the bag 14 in the area immediately adjacent the passageway.

In FIG. 8, it will be noted that nozzle 11 has four projecting ledges 19, 20, 21 and 22 which are spaced equidistantly from each other and peripherally around the end of the inlet 17 of nozzle 11. Preferably, the ledge members are in the form of shark's teeth which extend transversly from the longitudinal axis of the nozzle 11 as well as downwardly and inwardly toward the inlet 30 of passageway 28.

Another embodiment of the invention is shown in FIG. 9. Connection means 70 includes a nozzle 71 similar to nozzle 11 except that there are no projecting ledges adjacent the intake portion. In their place, there is provided a projecting section 72 which with flexible washer section 73 forms a groove 74 for engagement by projecting ledge 75. Sealing rings 77 and 78 resiliently contact the inlet end 80 of nozzle 71 between the flexible washer section 73 and wall section 82.

OPERATION

A better understanding of the advantages of connection means 10 and 70 will be had by a description of their operation. Turning to connection means 10 first, the nozzle 11 is utilized in conjunction with neck portion 26 of bag 14. Nozzle 11 will be packaged separately from bag 14 and bag 14 will preferably have an antiseptic powder material placed therein. An adhesive cap will be placed over the mouth 25 of neck 26. When it is desired to utilize the syringe unit 18 the adhesive cap will be removed from bag 14 and the head 38 of faucet 36 placed in neck portion 26 and against the flexible washer section 29. Liquid in the form of water 40 will then be filled into bag 14 as indicated in FIG. 1. When the desired amount of liquid 40 is placed therein, the bag 14 will be removed one use only and is completely disposable.

Referring to FIG. 7 it will be seen that when the unit is utilized, it may become necessary to stop the flow of liquid to the nozzle 11. This is easily facilitated by placing of the finger 34 against a portion of the flexible wall 24 of bag 14 and forcing it against the inlet of nozzle passageway 28. Simple withdrawal of the finger will subsequently permit liquid to flow into and out of nozzle 11 and radiating ports 60 in nozzle head 13. The flow to the ports 60 is through the hollow spray stem 15 and along channels 57 in hub 51.

Connection means 70 will form a syringe unit 85 and will be operable with a flexible bag 14 similar to unit 18. The basic difference will be in the manner in which nozzle 71 engages neck 76. All that is required to interconnect nozzle 71 with bag 14 is to place inlet end 80 of nozzle 71 into the passageway provided by neck 76 until projecting flange 75 seats in groove 74. Once so seated, it is extremely difficult to remove nozzle 71 as a tight friction fit is afforded by means of the resiliency of neck 76. At the same time a fluid tight engagement results due to the sealing of projecting ledge 75 on washer section 73 and sealing rings 77 and 78 engaging inlet end 80 of nozzle 71.

As indicated earlier, the syringe units 18 and 85 are completely disposable. The nozzles 11 and 71 and bag 14 are fabricated from polyethylene material. The neck portions 26 and 76 as well as washer sections 29 and 73 are also molded from polyethylene as well as the surrounding wall sections 27 and 82. Bag 14 is preferably formed as a separate unit and heat sealed to wall sections 27 and 82 which are integrally molded with necks 26 and 76. In a preferred manner, bag 14 is formed by sealling opposing sheets of plastic material together entirely around its periphery and then heat sealing the wall sections 27 and 82 of neck portions 26 and 76 to the bag preferably at the periphery of the bag so as to facilitate the valving action illustrated in FIG. 7.

While in the previous description, a particular nozzle head structure was described utilizing a hub 51 with ribs 53 and channels 57, it is not essential that this particular spray head be utilized. Instead, one could employ a nozzle with a multiplicity of apertures at the nozzle head with the head and the nozzle being a single unitary structure. Further, while four projecting ledges 19–22 are indicated for use with nozzle 11, any number of ledges could be utilized including two. They could be spaced in any geometric pattern. Preferably, they should be of the type which can be resiliently forced through the neck portion 26 to engage the inside of wall 27 once inside bag 14.

It will thus be seen that through the present invention there is now provided a unique connecting means for a disposable syringe unit wherein a fluid-tight engagement is provided between the nozzle and the bag. The connecting means affords a one-use-only feature for the syringe unit, yet at the same time permits fluid-tight engagement with the head of the faucet. The syringe unit and its connection means is easily molded from plastic materials thereby affording low cost. The syringe unit is easily assembled and affords a simple valving action if desired.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A disposable syringe having a flexible bag for containing fluid, said bag having only a single entrance that also provides a discharge exit, said syringe having an entrance portion sized and shaped to receive and retain a stem end of a hollow nozzle, the syringe and nozzle including:
   (a) a hollow nozzle of at least semi-rigid material and defining a hollow spray stem having an outlet end and an inlet end;
   (b) an outwardly extending ring-like portion formed integrally on said nozzle, said ring-like portion spaced a selected short distance from the inlet end and substantially normal to the axis of said stem, the downward facing surface of said ring-like portion being a shoulder surface substantially normal to the axis of said stem;
   (c) a plurality of discontinuous outwardly sprag-like tooth portions formed on said hollow nozzle and adjacent the inlet end of said nozzle, the upward facing surfaces of the sprag-like tooth portions having shoulder surfaces substantially normal to the axis of said stem;
   (d) a syringe bag having a flexible side wall terminating with a neck portion having a passage therethrough and whose outer entrance at the outlet end is flexible and provides a washer portion sized so as to receive a spout end of a filling faucet, said neck portion and the passageway therethrough having a resilient capability to at least partially deflect and pass the sprag-like tooth portions on said nozzle, the neck portion otherwise sized to slidably retain the stem of the nozzle, the neck portion where it joins the bag providing a wall that for at least a short distance forms a shoulder surface substantially normal to the axis through the neck portion, and
   (e) a groove formed in the neck portion of the bag and inwardly of the washer portion, this groove sized and shaped to receive and retain said outwardly extending ring-like portion formed on the nozzle, the upward facing surface of the groove providing a shoulder surface substantially normal to the axis through the neck portion whereby said inlet end of the nozzle is placed in the neck of the filled syringe and is manipulated to advance the nozzle and the sprag-like tooth portions through the neck portion so that the sprag-like end portion passes through the neck whereby the upwardly formed shoulders of the sprag-like portions engage the inner shoulder surface of the bag while said outwardly extending ring-like portion enters and is seated in said groove in the neck of the syringe bag, said selected distance from the downward facing surface on the ring-like portion of the stem and the upward facing surfaces of the sprag-like tooth portions also on said stem being sufficiently less than the upward facing surface of the groove in the neck portion and the shoulder surface provided by the wall of the bag next to the neck portion insures that the nozzle stem is retained and a fluid tight, resilient connection is provided between said nozzle stem and the neck of the bag and said nozzle is prevented by the sprag portions from removal from the neck passageway.

2. A disposable syringe and nozzle as in claim 1 in which the stem portion of the nozzle and the neck portion of the syringe bag are each of an annular configuration.

3. A disposable syringe and nozzle as in claim 1 in which the sprag-like tooth projections are four in number and are positioned equidistantly from each other.

4. A disposable syringe and nozzle as in claim 1 in which said neck portion includes sealing rings positioned to engage said nozzle inlet end between said projecting means.

5. A disposable syringe and nozzle as in claim 1 in which said flexible bag is composed of material sufficiently flexible and constructed and arranged to permit a finger of a human hand to press said bag from the outside against the entrance end of said nozzle member.

6. A disposable syringe and nozzle as in claim 1 in which said neck portion and said wall section surrounding neck passageway are formed initially as one piece and said bag is another.

7. A disposable syringe having a flexible bag for containing fluid, said bag having only a single entrance that also provides a discharge exit, said syringe having an entrance portion sized and shaped to receive and retain a stem end of a hollow nozzle, the syringe and nozzle including:
   (a) a hollow nozzle of at least semi-rigid material and defining a hollow spray stem having an outlet end and an inlet end;
   (b) an outwardly extending ring-like portion formed integrally on said nozzle, said ring-like portion spaced a selected short distance from the inlet end of the nozzle and substantially normal to the axis of said stem, the upper and lower surfaces of said ring-like portion being surfaces substantially normal to the axis of said stem;
   (c) a syringe bag having a flexible side wall terminating with a neck portion having a passage therethrough and whose outer entrance at the outlet end is flexible and provides a washer portion sized so as to receive a spout end of a filling faucet, said neck portion sized to slidably retain the stem of the nozzle, and
   (d) a groove formed in the neck portion of the bag and inwardly of said washer portion, this groove sized and shaped to receive and retain said outwardly extending ring-like portion formed on the nozzle in a fluid tight manner, said groove substantially normal to the axis through the neck portion whereby when said inlet end of the nozzle is placed in the neck of the filled syringe and is manipulated to advance the nozzle through the neck portion said nozzle stem passes through the neck, said end extends at least slightly below the neck portion of the syringe bag and into said bag when and while the ring-like portion of the nozzle stem is seated in said groove, the outwardly extending ring-like projection formed on the stem of the nozzle being sufficiently greater in width than the groove formed in the neck portion of said syringe bag so that in a seated condition the nozzle stem is retained with a fluid tight connection provided between said nozzle stem and the neck of the bag, the neck portion being sufficiently resilient to allow expansion thereof for introduction of the ring-like member of the stem into said groove and then returning of the neck portion substantially to its normal condition and position, the flexible material of the bag being constructed and arranged to permit a finger of a human hand to press said bag from the outside against the passageway of said nozzle member.

8. A disposable syringe and nozzle as in claim 7 in which said neck portion includes sealing rings positioned to engage said nozzle stem below the outwardly extending ring-like portion and the inlet end of the nozzle.

* * * * *

UNITED STATES PATENT AND TRADEMARK OFFICE
CERTIFICATE OF CORRECTION

PATENT NO. : 4,274,555
DATED : June 23, 1981
INVENTOR(S) : Vincent K. Sneider

It is certified that error appears in the above—identified patent and that said Letters Patent is hereby corrected as shown below:

Column 3, line 67, after "removed" insert --from faucet 36 and the inlet end 17 of the nozzle 11 will be seated in neck portion 26. The nozzle will be forced into neck 26 so that flange 23 will press against the flexible washer section 29. At the same time, projecting ledges 19, 20, 21 and 22 will seat themselves under the wall section 27. In this manner, a resilient engagement is provided between flange 23 and the washer section 29. As the projections 19 - 22 are in the form of shark's teeth, once they engage under wall 27, extreme force would be required to remove the nozzle from the bag. Accordingly, the bag 14 can be filled only once and utilized only once. It is therefore intended for---.

Signed and Sealed this

*First* Day of *September 1981*

[SEAL]

*Attest:*

GERALD J. MOSSINGHOFF

*Attesting Officer*   *Commissioner of Patents and Trademarks*